United States Patent [19]

Yost et al.

[11] Patent Number: 5,031,627

[45] Date of Patent: Jul. 16, 1991

[54] METHOD AND APPARATUS FOR CHARACTERIZING REFLECTED ULTRASONIC PULSES

[75] Inventors: William T. Yost, Newport News; John H. Cantrell, Jr., Tabb, both of Va.

[73] Assignee: The United States of America as represented by the Administrator of the National Aeronautics and Space Administration, Washington, D.C.

[21] Appl. No.: 422,726

[22] Filed: Oct. 17, 1989

[51] Int. Cl.[5] ............................................... A61B 8/00
[52] U.S. Cl. .................................. 128/660.06; 73/631
[58] Field of Search ...................... 128/661.03–661.07, 128/660.01, 660.06; 73/631

[56] References Cited

U.S. PATENT DOCUMENTS

4,043,181 8/1977 Nigam ................................. 73/631 X
4,080,960 3/1978 Goans et al. .................... 128/661.03
4,852,576 8/1989 Inbar et al. ......................... 73/631 X

Primary Examiner—Francis Jaworski
Attorney, Agent, or Firm—Harold W. Adams

[57] ABSTRACT

The invention is a method of and apparatus for characterizing the amplitudes of a sequence of reflected pulses $R_1$, $R_2$, and $R_3$ by converting them into corresponding electrical signals $E_1$, $E_2$, and $E_3$ and thereafter exponentially adjusting the amplitudes of the respective signals $E_1$, $E_2$, and $E_3$ to substantially the same value during each sequence thereby restoring the reflected pulses $R_1$, $R_2$, and $R_3$ to their initial reflection values by means of timing means 12 and 13, an exponential generator 17 and a time gain compensator 18. Envelope and baseline reject circuits 23 and 24 respectively permit the display and accurate location of the time spaced sequence of electric signals having substantially the same amplitude on a measurement scale on a suitable video display or oscilloscope 14.

20 Claims, 8 Drawing Sheets

METHOD AND APPARATUS FOR CHARACTERIZING REFLECTED ULTRASONIC PULSES

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

1. Field of the Invention

The invention is a method and apparatus for characterizing reflected ultrasonic pulses and more particularly to such method and apparatus for characterizing the amplitude of ultrasonic pulses reflected from discontinuities in living tissue including those resulting naturally and from trauma such as burns, wounds, scars, and surgery as well as in other ultrasonic sound wave propagation mediums in which the attenuation coefficient and velocity of reflected ultrasonic pulses remains substantially unchanged.

2. Description of the Prior Art

Generally, there are three types of so called degrees of burn wounds in human tissue—first, second, and third which are related to severity, diagnosis, and treatment. Briefly, first degree burns involve only the outer skin or epidermis, second degree burns extend into and through the dermis and third degree burns extend through both the epidermis and dermis into the subcutaneous layer of fat of the body.

It is generally believed that the respective layers of human tissue, the epidermis, dermis, and underlying layer of subcutaneous fat have different and detectable acoustical impedances which form interfaces or discontinuities therebetween that reflect ultrasonic sound waves and which layers are respectively altered when subjected to different degrees of burning or other trauma.

For example, see U.S. Pat. No. 4,080,960, dated Mar. 28, 1978, which discloses an ultrasonic echo method of determining burn depths by sensing an acoustic pulse reflected by the interface between burned and unburned human tissue. Also see U.S. Pat. No. 4,733,668, dated Mar. 29, 1988, which discloses an ultrasonic method and apparatus for examining human tissue including linear time gain amplification to compensate for differences in the attenuation of ultrasound energy in passing through human tissues having different attenuation characteristics.

Ultrasonic diagnostic instruments are generally known that compensate for the change of attenuation of an ultrasonic pulse reflected from a discontinuity detected in living human tissue by employing linear time gain circuitry as described in U.S. Pat. No. 4,733,668. It is also a known scientific principle that the attenuation of an ultrasonic pulse in passing through a given propagation medium is exponential. Ultrasonic pulse-echo apparatus including exponential time gain compensation has been generally proposed to compensate for such attenuation. For instance, see U.S. Pat. No. 4,043,181 dated Aug. 23, 1977.

With or without the gain compensation of the prior art, techniques to detect ultrasonic reflections in human tissue and visually display them on a suitable oscilloscope with accuracy and resolution for diagnostic purposes is difficult because of variations in attenuation introduced by aging, color, composition, sex, and the many discontinuities or interfaces in human tissue that also substantially change the attenuation as well as velocity of the reflected pulses.

The latter produces a clutter of reflected pulses all of which are subjected to the particular time gain compensation, if any, prior to being displayed in typically an A-scan. The value or size of the amplitude of the respective reflected pulses is meaningless in conventional systems. Typically, the clutter of reflected pulses in such A-scans makes it difficult to clearly identify and accurately locate reflected pulses of interest on the X or time axis, except by a skilled interpreter. Thus, even knowing the pulse velocity, conventional ultrasonic echo measurement and display systems do not accurately measure and display the distance of the discontinuity causing the reflection from the source of ultrasonic pulses-a critical determination is burn depth monitoring or scanning.

Thus, the type, linear or exponential, of prior art gain compensation used in processing the reflected pulses in conventional ultrasonic pulse echo diagnostic methods and circuitry is not used to characterize the amplitude of selected reflected pulses to accurately determine their point of origin within a propagation medium such as human tissue.

OBJECT AND SUMMARY OF THE INVENTION

It is known that whenever ultrasound encounters an impedance discontinuity in its medium of propagation, some of the energy is reflected. For example, the most prominent reflections of ultrasonic pulses in undamaged human skin occur at a typical transducer coupling water-skin interface, at the burned-unburned tissue interface in the event of a burn, and at the dermis-fat interface as shown in U.S. Pat. No. 4,080,960. Other less prominent reflections also result from other structures and interfaces within the skin—for instance, the epidermis-dermis interface. These many reflections result from the laws of physics as applied to the wave motion of sound in a propagation medium, such as the reflections of light from the interface between glass and air.

A significant property of the medium in which ultrasound passes is called impedance. It is the product of sound velocity and the density of the medium.

$$Z = \rho V \qquad (1)$$

where $Z$ = the impedance of the medium
$\rho$ = the density of the medium
$V$ = the velocity of sound in the medium.

Variation in either of these quantities can change the impedance of the medium. As long as the impedance of the medium remains constant, however, the ultrasound will travel through it, without reflection, just as light travels, unimpeded, through air.

Another significant property of a propagation medium is the attenuation coefficient which is generally expressed as:

$$A_o = \frac{1}{X} \log_o \frac{A_o}{A} \qquad (2)$$

where
$X$ is the distance of wave propagation in the medium $A_o$ is the amplitude, at the origin A is the amplitude of the wave at the distance, X.

Whenever there is an abrupt change of the impedance creating a discontinuity or interface in the path of the ultrasound, some energy is reflected, just as light is reflected from a glass-air interface. The ratio of the amplitude of the reflected ultrasonic wave to the amplitude of the incident ultrasonic wave can be predicted from the equation $$A_r/A_i = (Z_2 - Z_1)/(Z_2 + Z_1) \quad (3)$$

where $A_r$ = the amplitude of the reflected wave
$A_i$ = the amplitude of the incident wave
$Z_1$ = the impedance of the first medium
$Z_2$ = the impedance of the second medium.

By measuring the sound velocities and the densities of the two media, the reflection factor, $(Z_2 - Z_1)/(Z_2 + Z_1)$ can be predicted. Using this and knowing the amplitude of the incident wave, the amplitude of the reflected wave can be calculated.

Assume that ultrasound encounters and travels through viable skin tissue. Also assume that the ultrasound impinges on the skin surface after passing through a coupling medium such as water. Some of the sound is reflected from the interface between the water and the front surface of the skin as a pulse $R_1$. Using values for the respective impedances, it has been found that the reflected wave amplitude of the pulse $R_1$ is in the neighborhood of 0.09 of the initial amplitude. The rest of the sound continues traveling through the skin.

Other reflections can result from various structures within the skin. In general, these reflections are small, and, except for a weakening of the ultrasound, are negligible. However, when the remaining ultrasound impinges on an intervening burn-unburned tissue interface and finally the dermis-fat interface, two additional major reflections $R_2$ and $R_3$ result.

It has been discovered as explained hereinafter, that due to the relationship between the acoustic impedance discontinuities at the respective interfaces, the amplitudes of the reflected pulses $R_1$, $R_2$, and $R_3$ are substantially equal and that the rate of attenuation and velocity of the pulses $R_1$, $R_2$, and $R_3$ remain substantially unchanged. This results in a sequence of reflected ultrasonic pulses $R_1$, $R_2$, and $R_3$ which are of near equal height at the instant of reflection, neglecting the effects of scattering and other losses which attenuate the ultrasound.

Applying the principals of the invention, the resulting reflected ultrasonic pulses $R_1$, $R_2$, and $R_3$ may be characterized in novel processing circuitry by exponentially adjusting the amplitudes of corresponding sequences of electrical signals $E_1$, $E_2$, and $E_3$ to substantially the same and equal value of the amplitudes of the reflected pulses $R_1$, $R_2$, and $R_3$ at the instant of reflection. Only the compensated and corresponding electrical signals $E_1$, $E_2$, and $E_3$ are thereafter displayed. This characterization of the amplitude of the reflected pulses thus permits the accurate location and display of only the impedance discontinuities of interest.

By knowing the velocity of sound in skin, one can determine the thickness of the skin by using the relationship $$X = Vt/2 \quad (4)$$

where X = skin thickness

V = velocity of sound for skin
t = time interval between the 2 pulses, $R_1$ and $R_3$.

It is known that when skin suffers a burn injury, there is a change in the impedance of the region between the front surface and the necrotic-viable skin interface. The inventors have discovered and believe that this change in acoustic impedance is caused by the change in the density of the necrotic region which results from uncoiling of collagen in the burned tissue and effects associated with it. A skin burn thus can produce two regions of different acoustic impedance within the skin itself.

It has also been discovered that the resulting acoustic impedance ratio at a burn-unburned tissue interface that causes pulse $R_2$ is substantially the same as the impedance ratios at the interfaces between the ultrasonic coupling (water or the like) and the skin surface that causes $R_1$ and the interface between unburned tissue (dermis) and the underlying layer of fat that causes $R_3$. As also discovered there is substantially no change in velocity or the coefficient attenuation of the pulses $R_1$, $R_2$, $R_3$, and $R_s$ in the propagation medium. Therefore, the actual attenuation of the pulses $R_1$, $R_2$, and $R_3$ is determined by an exponential function which as hereafter explained is directly related to the age of the human tissue examined and other factors.

Assuming a large reflection $R_1$ (neglecting effects of attenuation approximately 0.09 of the original amplitude) occurs from a water-necrotic skin interface, a large reflection $R_2$ (neglecting effects of attenuation approximately 0.07 of the amplitude of the wave reaching the interface) occurs from a necrotic-viable skin interface, and that a third major reflection occurs $R_3$ from the dermis-fat interface (neglecting effects of attenuation approximately 0.07 of the amplitude of the wave reaching this interface) are received and corresponding electrical signals displayed, the remaining viable skin thickness can be calculated by $$X = V(t_3 - t_2)/2 \quad (5)$$

where $(t_3 - t_2)$ = time interval between the received pulses $R_2$ and $R_3$.

In addition to the major pulses mentioned above, other structures cause apparent reflections in necrotic skin tissue. This is caused by the formation of sub regions, each with different impedances and attenuation coefficients. The smaller reflections from irregularly shaped boundaries between these subregions can also scatter substantial energy from the ultrasonic wave. By applying the principles of this invention to characterize and preserve the relative size of the reflected pulses $R_1$, $R_2$, and $R_3$, the necrotic region can be more accurately located and displayed since the viable tissue region will not cause as much scattering between pulses $R_2$ and $R_3$.

For full thickness burn wounds through the dermis there are only two reflections: $R_1$ from the water-necrotic tissue interface, and $R_2$ from the necrotic dermis-fat interface with substantially higher scattering of ultrasound than occurs in unburned tissue.

While the impedance discontinuities of interest described thus far are those between unburned and burned skin in the epidermis and dermis and underlying fat in living tissue, the invention may be used to characterize acoustic pulses from discontinuities in other propagation mediums in which the impedance ratios at the respective discontinuities are the same and the velocity and attenuation coefficient of the propagation medium remains substantially unchanged.

An object of the invention is to provide method and apparatus for characterizing the amplitude of ultrasonic pulses reflected from impedance discontinuities having the same reflection coefficient in a propagation medium in which the attenuation coefficient and velocity of said reflected pulses remains substantially unchanged.

Another object of the invention is to provide method and apparatus for characterizing the amplitude of ultrasonic pulses reflected from a necrotic-viable skin interface in human tissue irrespective of the age of the human tissue that may range from "young" to "old" and vary in color, composition, sex, and other factors.

Still another object of the invention is to provide method and means for selectively processing ultrasonic pulses of up to 60 MHz and higher reflected in burned human tissue to effectively restore and display the reflected ultrasonic pulses at their respective reflection amplitudes thereby accurately locating any interfaces between necrotic and viable skin in said human tissue irrespective of the age, color, composition, and sex of the person examined.

Yet another object of the invention is to provide method and means for characterizing ultrasonic pulses having a selected center frequency and reflected in a propagation medium in which the attenuation coefficient and velocity of said reflected pulses therein remains substantially unchanged by effectively restoring the amplitudes of said reflected ultrasonic signals to their initial, calculable and substantially the same value.

A further object of the invention is to provide method and means for measuring the thickness of different types of burns in human tissues ranging in age from "young" to "old" and other factors to a resolution of approximately 26 microns (0.026 mm) of skin thickness.

The above and other objects may be achieved by the invention which may include the steps of: transmitting ultrasonic pulses from a focused transducer having a selected center frequency of up to 50 MHz or more through a suitable coupling into a propagation medium such as human skin formed of distinct layers of epidermis, dermis and subcutaneous fat tissues; receiving a sequence of ultrasonic pulses including $R_1$ and $R_3$ reflected from impedance discontinuities at said coupling-epidermis and said dermis-fat layer interfaces respectively and intermediate ultrasonic pulses $R_2$ reflected from a necrotic-unburned tissue interface in the dermis layer; processing and displaying on a measurement scale a sequence of electric signals $E_1$, $E_2$, and $E_3$ corresponding to said sequence of pulses $R_1$, $R_2$, and $R_3$; adjusting the amplitude of the displayed signal $E_1$ to an initial level; and thereafter characterizing the amplitudes of the sequence of ultrasonic pulses $R_1$, $R_2$, and $R_3$ to compensate for change in the attenuation coefficient of the human tissue examined resulting from age, color, composition, sex, and other factors by exponentially and simultaneously adjusting the amplitudes of displayed signals $E_3$ and $E_2$ to substantially equal the amplitude of displayed signal $E_1$ thereby accurately locating and displaying the necrotic-unburned tissue interface in said dermis layer on said measurement scale irrespective of the attenuation coefficient of said human tissue.

Circuitry for receiving the ultrasonic pulses $R_1$, $R_2$, and $R_3$ and processing and displaying corresponding and characterized electrical output signals $E_1$, $E_2$ and $E_3$ may include first and second timing circuit means responsive to a main ultrasonic pulse from a focused transducer to simultaneously actuate a video display and an adjustable exponential generator used for characterizing the amplitudes of corresponding electrical output signals $E_1$, $E_2$, and $E_3$ of a time-gain compensator which exponentially adjusts the amplitudes of the output signals $E_1$, $E_2$, and $E_3$ over a calculable range for a given center frequency to a selected and substantially equal value thereby compensating for those factors determinative of the attenuation coefficient of the human tissue examined including age, color, composition, and sex. Suitable envelope and baseline reject circuitry permit the display of a time spaced sequence of characterized electric signals for $E_1$, $E_2$, and $E_3$ having substantially the same amplitude on a measurement scale in the video display.

BRIEF DESCRIPTION OF THE DRAWINGS

The above and numerous other objects and advantages will become apparent from the following Description of a Preferred Embodiment of the Invention when read in view of the appended drawings wherein.

BRIEF DESCRIPTION OF THE INVENTION

The quantitative assessment of burn depth in diagnosing and treating victims having severe thermal injury remains a challenging problem facing burn surgeons. Notwithstanding the advances in the prior art previously discussed, a high resolution, ultrasonic system capable of the accurate measurement and display of the depth of skin burns within five percent or less of the depth values obtained independently from histological sections is not commercially available. This invention achieves such accuracy which is within surgical requirements and thus provides an objective ultrasonic method and means to diagnose burn injuries as a practical alternative to current ultrasonic techniques and subjective diagnostic methodologies.

Figure 1:
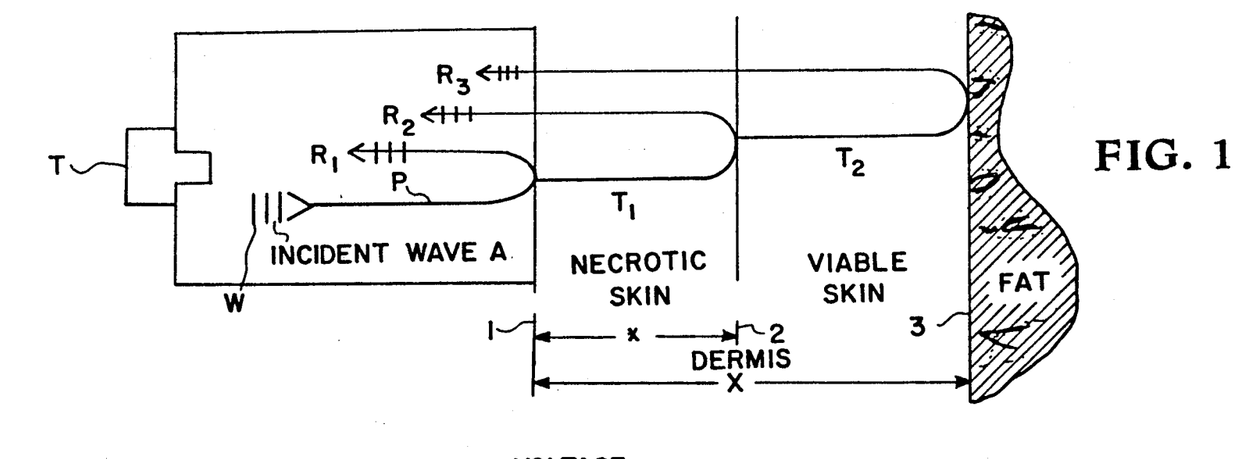
FIG. 1 is a diagram illustrating the transmission of ultrasonic pulses from a focused transducer into and reflection from human skin formed by an outer layer of epidermis, a second inner layer of dermis, and a third subcutaneous layer of fat.

To understand the principles of the invention it is important to consider what happens to the acoustic parameters of human skin when subjected to flame, scalding, and chemical burns. A thermal burn such as illustrated in FIG. 1 causes a change in the acoustic impedance of the irreversibly damaged or necrotic region between the skin surface plane (epidermis) and a plane identified as burn-interface. Thus, burned skin forms a sequence of planes 1, 2, and 3 or interfaces separating regions of different acoustic impedances, each plane 1, 2, and 3 marking an acoustic impedance discontinuity.

In FIG. 1 planes 1, 2, and 3 are at the skin surface, the burn interface, and the dermis-fat interface, respectively. It has been discovered that the burn interface at plane 2 is most probably caused by the uncoiling of collagen in the necrotic tissue which results in a change in density of the necrotic tissue. This, it can be calculated, gives rise to a reflection $R_2$ of approximately ten percent of the acoustical pulse that passed through plane 1. As it was found that reflections $R_1$ and $R_3$ of about the same amount amplitude occur from planes 1 and 3, it was then discovered that the reflected pulses $R_1$, $R_2$ and $R_3$ from the three interfaces can be calculated by making certain assumptions about human skin characteristics such as age, color, sex, densities, ultrasonic velocities, and the resulting ultrasonic attenuation coefficient in necrotic and viable skin tissue. These calculations led to the conclusion that by neglecting attenuation effects, the three pulses $R_1$, $R_2$, and $R_3$ are characterized in that their respective amplitudes are substantially equal at the instant of reflection irrespective of the age of the skin in which reflected. This amplitude value however varies over a calculable age range from "young" to "old" determined by the center frequency of the reflected pulses $R_1$, $R_2$, and $R_3$.

For example, assume a main pulse P with an amplitude A from a transducer T establishes the sequence of reflected pulses $R_1$, $R_2$, and $R_3$. Using typical values for human skin and assuming the velocities and attenuation of the pulses $R_1$, $R_2$, and $R_3$ are equal, the values of the amplitudes of the reflected pulses $R_1$, $R_2$, and $R_3$ in order of their reception are 0.09 A; 0.07 A $\exp^{-a_D x}$; and 0.07 A $\exp^{-a_D X}$, where x and X are the distances from the front surface of the epidermis (plane 1) to the burn interface (plane 2) and the dermis-fat interface (plane 3) respectively. Thus the amplitudes of the three pulses $R_1$, $R_2$, and $R_3$ at the instant of reflection are substantially equal, the slight difference being statistically insignificant due to the standard deviation of each acoustic impedance from which the calculations are made.

Figure 2:
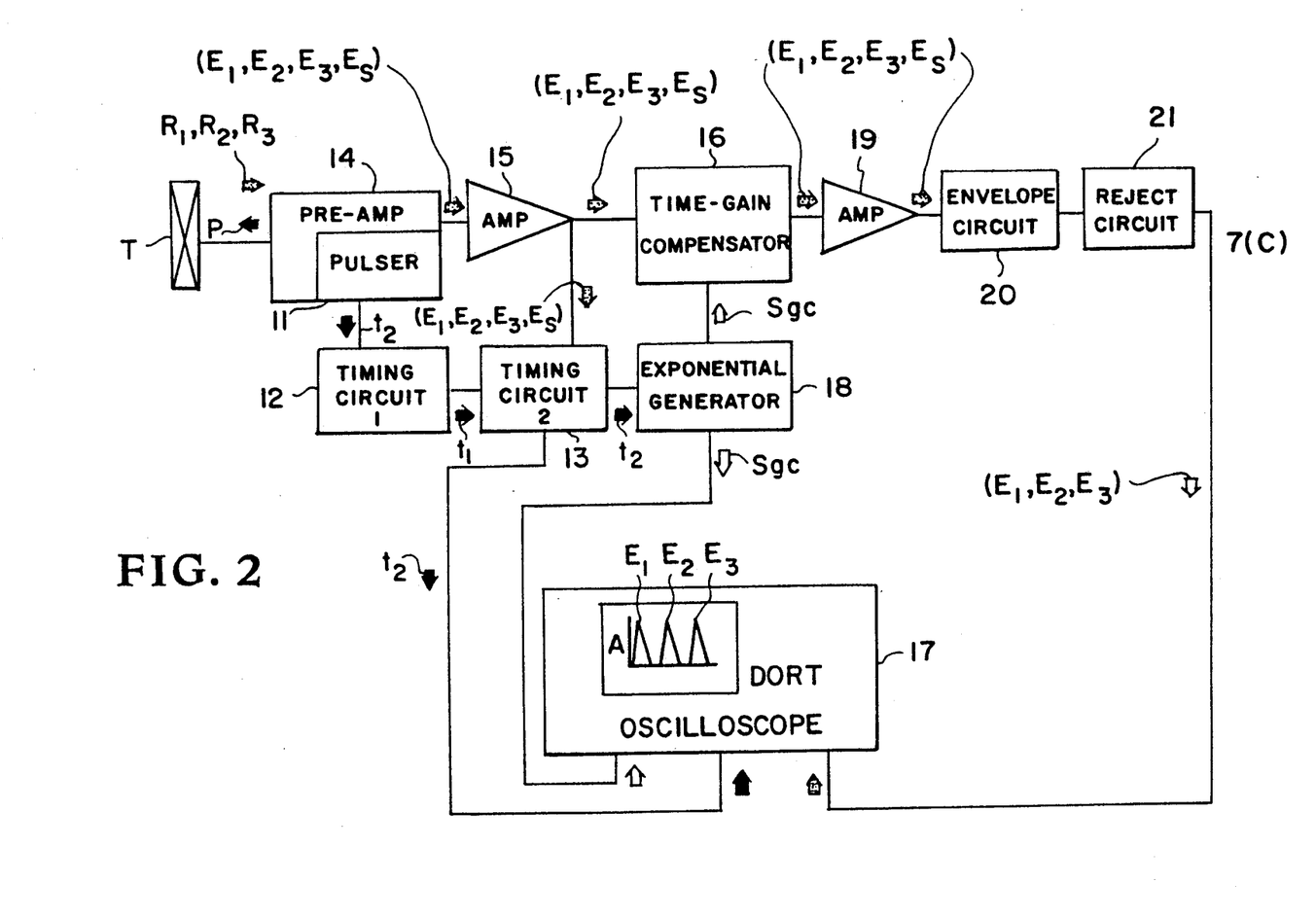
FIG. 2 is an electrical schematic embodying the invention used for characterizing ultrasonic pulses reflected in human tissue.

As shown in FIG. 2 and in accordance with the invention, after their reception, the sequence of pulses $R_1$, $R_2$, and $R_3$ are converted into corresponding electrical signals $E_1$, $E_2$, and $E_3$ which are passed through a time gain compensation (TGC) circuit 16 adjustably set to exponentially increase the amplification of the sequence of electrical signals $E_1$, $E_2$, and $E_3$ over a predetermined range until their respective amplitudes A are substantially equal as shown by the calculated values.

Figure 7A:
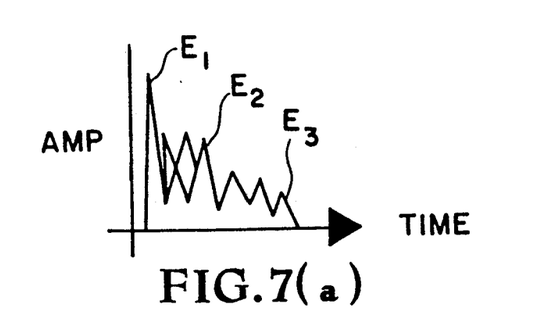
FIGS. 7A, B, and C illustrate a sequence of electrical signals $E_1$, $E_2$, and $E_3$ corresponding to reflected pulses $R_1$, $R_2$, and $R_3$ without and with pulse amplitude characterization in accordance with the invention.

This processing and calculated characterization of the reflected pulses $R_1$, $R_2$, and $R_3$ electronically and effectively removes or compensates for their attenuation in traveling through burned and unburned human skin as shown in FIG. 1. Thus, when the sequence of pulses $R_1$, $R_2$, and $R_3$ are characterized in accordance with the invention, the corresponding sequence of electrical signals $E_1$, $E_2$, and $E_3$ are all of substantially the same amplitude A as shown in FIGS. 7(B) and 7(C), having been calculated as follows:

| Pulse | Timing | Magnitude | TGC | Display |
|---|---|---|---|---|
| 1 | First | 0.09 A | 1 | 0.09 A |
| 2 | Second | 0.07 A$\exp_D^{-2a x}$ | $\exp_T^{+a t}$ | 0.07 A |
| 3 | Third | 0.07 A$\exp^{-2a_D X}$ | $\exp_T^{+a T}$ | 0.07 A |

($a_T = V a_D$ where V = velocity of ultrasound).

Figure 7B:
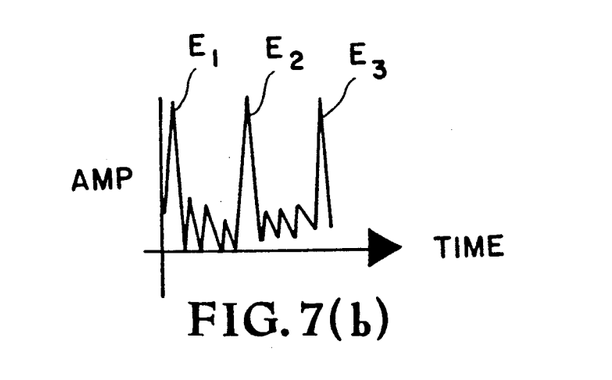
Figure 7C:
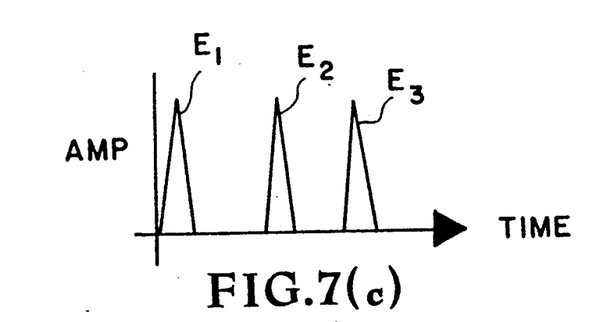

As shown in FIG. 7(B), an A-scan display, $E_1$, $E_2$, $E_3$ are all substantially higher than the pulses caused by other impedance discontinuities such as sweat glands, hair follicles and other structures not related to the impedance discontinuity of interest represented by pulse $R_2$ and the corresponding signal $E_2$—the burn-viable dermis interface.

Figure 5:
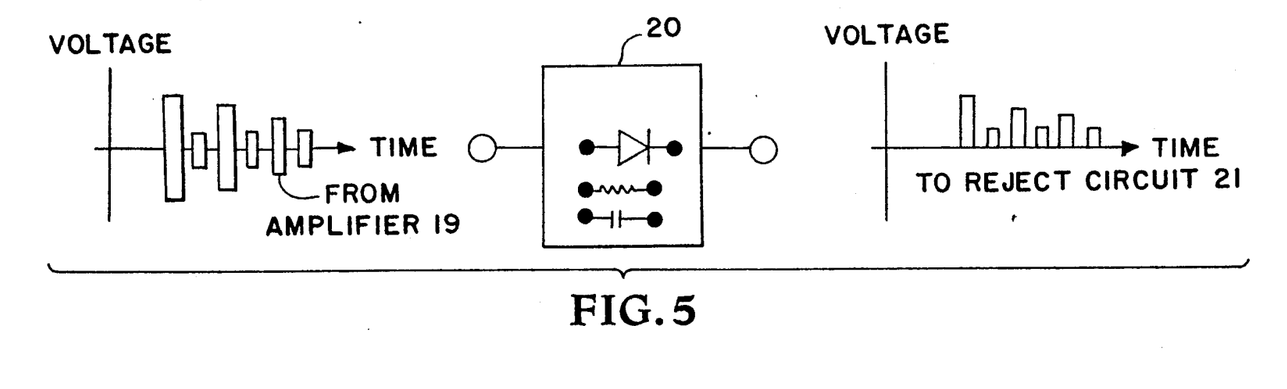
FIG. 5 is a schematic illustrating the envelope circuitry of FIG. 2 in greater detail.
Figure 6:
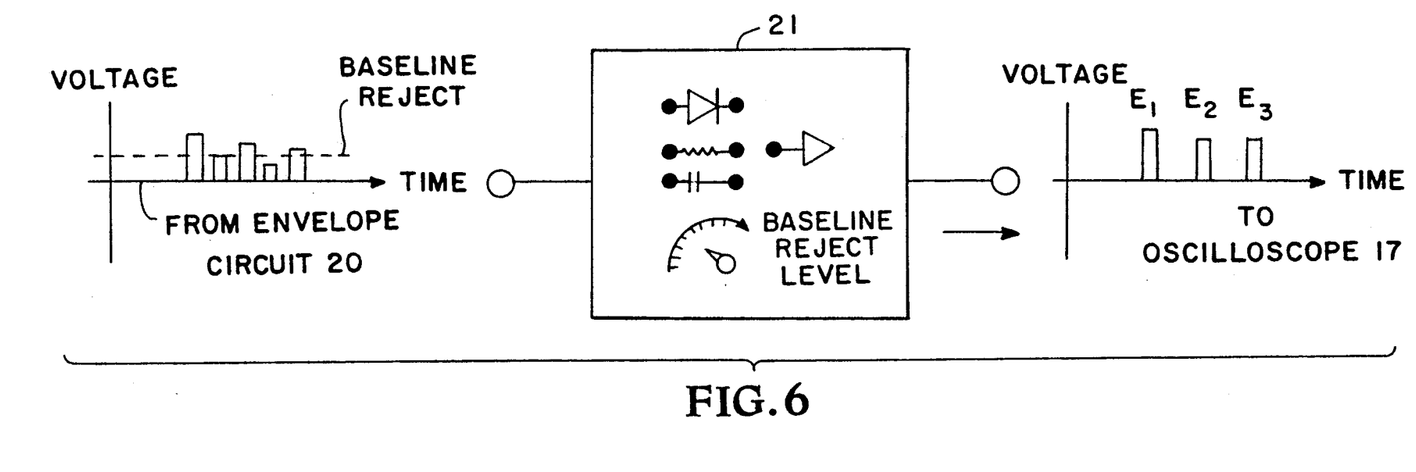
FIG. 6 is a schematic illustrating the reject circuitry of FIG. 2 in greater detail.

The unwanted pulses, because of the greater amplitude A or height of the signals $E_1$, $E_2$, $E_3$ are discarded using conventional envelope and baseline discriminator circuitry as shown in FIGS. 5 and 6.

In the event there are unwanted reflections detected of greater amplitude signifying a discontinuity having a higher coefficient of reflection, the transducer may be scanned over the skin surface until the unwanted reflections are no longer detected and displayed.

Also, initially the gain of signal $E_1$ (pulse $R_1$) from an unburned skin surface may first be readjusted to an easily discernible level prior to setting the gain of $E_3$ (pulse $R_3$). Thereafter, as the transducer T is scanned over burned skin, the amplitude of signal $E_2$ is automatically and exponentially adjusted at the same rate to substantially the same value as that of $E_1$ and $E_3$.

Having thus effectively restored the reflected pulses $R_1$, $R_2$, and $R_3$ to their initial reflection amplitude, the corresponding electrical signals $E_1$, $E_2$ and $E_3$ may be used to clearly and accurately locate and display the time spacing between the three pulses $R_1$, $R_2$, and $R_3$. Knowing the velocity of the pulses $R_1$, $R_2$, and $R_3$, (about $1.540 \times 10^5$ cm/sec) the depth of a burn can be accurately displayed on a suitable measuring scale on the time axis of the oscilloscope as shown in FIG. 2.

As explained, in characterizing the amplitudes of the reflected pulses $R_1$, $R_2$, and $R_3$ by calculating and restoring them to their respective and substantially equal reflection amplitudes A, the following assumptions are made concerning ultrasonic reflections from the three planes or interfaces: (1) impedance differences depend only on density differences; (2) the attenuation coefficient is approximately the same for necrotic skin and viable skin; (3) the velocities of ultrasound in necrotic and viable skin are equal; and the attenuation in the transducer coupling (water bath typically) is small or negligible.

In addition, and as previously mentioned the gain or amplitudes A of the corresponding electrical signals $E_1$, $E_2$ and $E_3$ are exponentially increased over a predetermined range. This range is determined by the center frequency of the ultrasonic pulses $R_1$, $R_2$, and $R_3$ and the attenuation coefficient which exponentially varies over a range of values from $a_D = 5.5 \, f^{0.612}$ in "young" skin to $a_D = 1.2 \, f^{0.68}$ in "old" skin.

Predetermined ranges of exponential time-gain compensation required for reflected pulses $R_1$, $R_2$ and $R_3$ at selected center frequencies determined by the focused transducer T employed have been calculated based on skin type and age from "young" to "old" as follows:

| Frequency (in MHz) | Time-gain Compensation (dB/μs) |
|---|---|
| 10 | 0.86–3.38 |

-continued

| Frequency (in MHz) | Time-gain Compensation (dB/μs) |
| --- | --- |
| 15 | 1.14–4.30 |
| 20 | 1.38–5.16 |
| 25 | 1.61–5.91 |
| 30 | 1.82–6.62 |
| 40 | 2.21–7.88 |
| 50 | 2.58–9.03 |

Thus assuming ultrasonic pulses $R_1$, $R_2$, and $R_3$ from a focused transducer T having a center frequency of 50 MHz are reflected from three interfaces in human skin as shown in FIG. 1, the amplitude of the corresponding electrical signal $E_1$ shown in the display is adjusted to a convenient, easily discernible height or amplitude A to establish an exponential adjustment starting point or base value $E_1$. Then starting with the arbitrary base value of the amplitude A of signal $E_1$ as the lowest end of the predetermined range of 2.58–9.03 dB/μs, the gain or amplitudes A of the signals $E_1$, $E_2$, and $E_3$ are exponentially adjusted over time through the predetermined range until the amplitudes of the displayed signals $E_1$, $E_2$, and $E_3$ are substantially equal thereby compensating for any variation in attenuation due to the age of the skin in which the depth of a burn is to be measured while at the same time characterizing the amplitudes of the reflected pulses $R_1$, $R_2$, and $R_3$.

It is known that the resolution and thus the accuracy of the display in circuits of this type depend upon the frequency response of the focused transducer T used. In general, the higher the frequency of the transducer T the greater the resolution. This can lead to a greater amount of clutter caused by reflected and scattered waves from other structures in human skin giving rise to difficulty in interpreting conventional displays such as shown in FIG. 7(A).

By exponentially adjusting over time the gains of the electrical signals $E_1$, $E_2$, and $E_3$, to make them substantially equal, in accordance with the invention, any increase in clutter caused by an increase in transducer frequency can be removed using available envelope and baseline signal rejection techniques as shown in FIGS. 5 and 6.

Thus, the resulting characterization of the reflected pulses $R_1$, $R_2$ and $R_3$ of interest in accordance with the method of this invention permits the use of transducers T having a higher frequency response thus achieving greater resolution and accuracy in locating and displaying the depth of burns in human skin.

FIG. 2 illustrates a preferred embodiment of an electrical circuit for practicing the invention while FIGS. 3–6 illustrate features of FIG. 2 in greater detail. In general, the invention includes a focused transducer T having a selected center frequency for transmitting the main pulse P and receiving the sequence of reflected pulses $R_1$, $R_2$, and $R_3$. The center frequency of the transducer T may be 50 MHz or greater as previously explained.

A large voltage spike S generated by a pulser 11 is applied to transducer T causing it to transmit a main or incident ultrasonic pulse P into the region of a burn in human skin through a suitable coupling medium such as a waterbath W which substantially matches the acoustical impedance of the epidermis of the tissue into which transmitted and from which reflected as pulses $R_1$, $R_2$ and $R_3$ as illustrated in FIG. 1.

Simultaneously, the pulser sends a timing signal t to activate a first timing circuit means 12 which after a suitable delay (approximately the time from initiation of timing signal t until the first pulse $R_1$ of the sequence of reflected pulses $R_1$, $R_2$, $R_3$, and $R_s$ is received) as shown in FIG. 1 sends a timing signal $t_1$ which enables a second timing circuit means 13. The levels of signals $E_1$, $E_2$, $E_3$, and $E_s$ are amplified in an amplifier 14 and a booster amplifier 15 before passing into a time-gain compensator 16 as a timed sequence of signals as shown in FIG. 7(A) and being applied to timing circuit means 13.

When thus enabled and upon receipt of the leading edge of signal $E_1$ of the amplified sequence of electrical signals $E_1$, $E_2$, $E_3$ and $E_s$, as shown in FIG. 7(A) and which correspond to reflected pulses $R_1$, $R_2$, $R_3$, and $R_s$. The second timing circuit means 13 emits trigger pulses $t_2$ to start an oscilloscope 17 and an exponential generator 18.

The time-gain compensator 16 multiplies the timed sequence of electrical signals $E_1$, $E_2$, $E_3$, and $E_s$ with the output of the exponential generator 18. This multiplication process exponentially adjusts the gain of the signals over the calculated range for the center frequency of transducer T to the level required to compensate for attenuation losses in the reflected pulses $R_1$, $R_2$, and $R_3$ due to changes in the attenuation coefficient of human tissue caused by differences in age, color compensation, sex, and other factors in human tissue as previously explained.

For example, assuming a focused transducer T having a center frequency of 50 MHz is used, the exponential time gain compensation in dB/us has been calculated to be from 2.58–9.03 over a range of different types of human tissue varying in age from "young to old".

By characterizing or exponentially adjusting the amplitude of the signal $E_3$ over the aforementioned time-gain compensation range until it substantially equals the amplitudes of the respective electrical signals $E_1$ and $E_2$ (assuming there is a burn-unburned skin interface between signals $E_1$ and $E_3$) the circuit automatically compensates for variations in the attenuation coefficient of human tissue caused by age, color, sex, composition, and other factors.

By thus characterizing the amplitudes of the electrical signals $E_1$, $E_2$, and $E_3$ in this fashion, the reflector pulses $R_1$, $R_2$, and $R_3$ are effectively restored to their respective and substantially equal amplitudes at the instant of reflection. This exponential time-gain compensation permits the use of transducers T having a higher frequency response thus achieving greater resolution and accuracy in locating and displaying impedance discontinuities in a propagation medium such as the depth of a burn in human skin.

After further amplication and buffering in amplifier 19, the signals $E_1$, $E_2$, $E_3$, and $E_s$ are rectified in an envelope circuit 20 shown in greater detail in FIG. 5 after which the accompanying unwanted smaller signals $E_s$ are removed in a conventional baseline reject circuit 21 shown in greater detail in FIG. 6 before being displayed as an A-scan as shown in FIG. 7(c) on the screen of the oscilloscope 17.

As generally known, conventional ultrasonic medical diagnostic instruments operate in a frequency range from 1 to 10 MHz. Consequently, the resolution and thus accuracy of the typical display is inadequate for the examination of skin thicknesses requiring a resolution of approximately 26 microns (0.026 mm). This requires the electronic components of the circuit illustrated in FIG. 2, including the display oscilloscope 17 to have a frequency response of at least 60 MHz when using focused transducers T having center frequencies up to 50 MHz and greater.

While unfocused transducers are used in many prior art ultrasonic diagnostic circuits, focused transducers T as used in the invention are preferred because of their superior capabilities in detecting the often uneven and irregular necrotic-viable interfaces present in burned human tissue.

Using a modular design as shown in FIG. 2, permits each module of the circuit to be optimized for its specific purpose to assure that its respective performance is adequate. For instance, a Metrotek MR-106, with a Metrotek PR106 pulser-preamplifier-line driver manufactured by Stavely NDT Technologies of Richmond, Washington, used with a Tektronix power source from the TM-500 series manufactured by Tektronix Corporation of Beaverton, Oregon, serve as the module illustrated as the pulse R11 and preamplifier 14 in FIG. 2.

Figure 3:
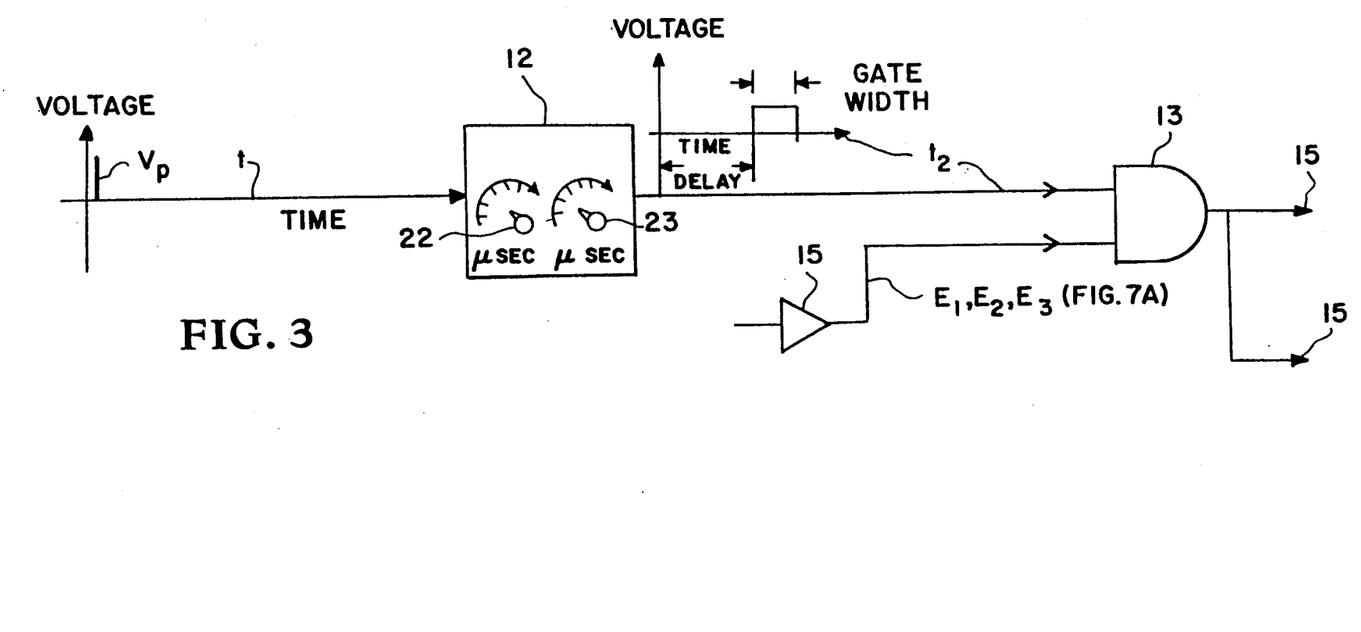
FIG. 3 is a schematic illustrating the timing circuits of FIG. 2 in greater detail.

Timing of the system is effected by the timing circuit means 12 and 13 and which are shown in greater detail in FIG. 3. As explained, a timing voltage pulse t coincident with the main pulse P triggers the timing circuit 12 to initiate the time delay determined by an adjustable control 22 prior to generating a gate signal $t_1$ which arms the timing circuit 13. The width of the gate signal $t^1$ may be adjusted by a suitable control 23. Once armed, the second timing circuit 13 waits for the sequence of amplified electrical signals $E_1$, $E_2$, $E_3$, $E_s$ from amplifier 15 at which time it simultaneously applies a trigger signal $t_2$ to both the oscilloscope 17 and the exponential generator 18. The oscilloscope 17 which may be a Hewlett-Packard model 741A storage oscilloscope manufactured by Hewlett-Packard Corporation of Palo Alto, California has a fast rise time assured by a 100 MHz frequency response. The oscilloscope 17 stores the display traces of the electrical signals $E_1$, $E_2$, $E_3$, and $E_s$ long enough to permit a photographic record to be made using a conventional oscilloscope camera.

The overall sensitivity of the circuit to the reflected ultrasonic pulses $R_1$, $R_2$, $R_3$, and $R_s$ is determined by the gain of amplifier 15 which may be adjustable over a range from $-10$ dB to $+60$ dB in dB switch selectable increments. It is important that the gain added by amplifier 15 offset the following time-gain compensation and baseline-reject conditioning of the corresponding electrical $E_1$, $E_2$, and $E_3$.

Because much of the energy of high frequency ultrasound is lost as it traverses the skin, it is necessary to restore the levels of the amplitudes A of the reflected ultrasonic pulses $R_1$, $R_2$, and $R_3$ to their initial reflection values. The time-gain compensator 16 under the control of output signals Sgc from the exponential generator 18 effects this compensation by exponentially increasing the gain of the time gain compensator 16 over the time interval of interest as detemined by the timing circuit means 12 and 13.

Such an adjustment is analogous to increasing the volume of a TV set in one millionth of a second when operating at a circuit frequency resolution of 60 MHz and is achieved by incorporating a conventional high speed multiplier and amplifier 30 with a 60 MHz frequency response and a dynamic range of 60 dB in the time gain compensator 16. The respective sequences of electrical signals $E_1$, $E_2$, $E_3$, and $E_s$ are multiplied by an amount determined by the resulting exponential ramp input signal Sgc from the exponential generator 18 which corresponds to the calculated reflection amplitudes of the reflected pulses $R_1$, $R_2$, $R_3$, and $R_s$ over the time interval between the signals $E_1$ and $E_3$.

Figure 4:
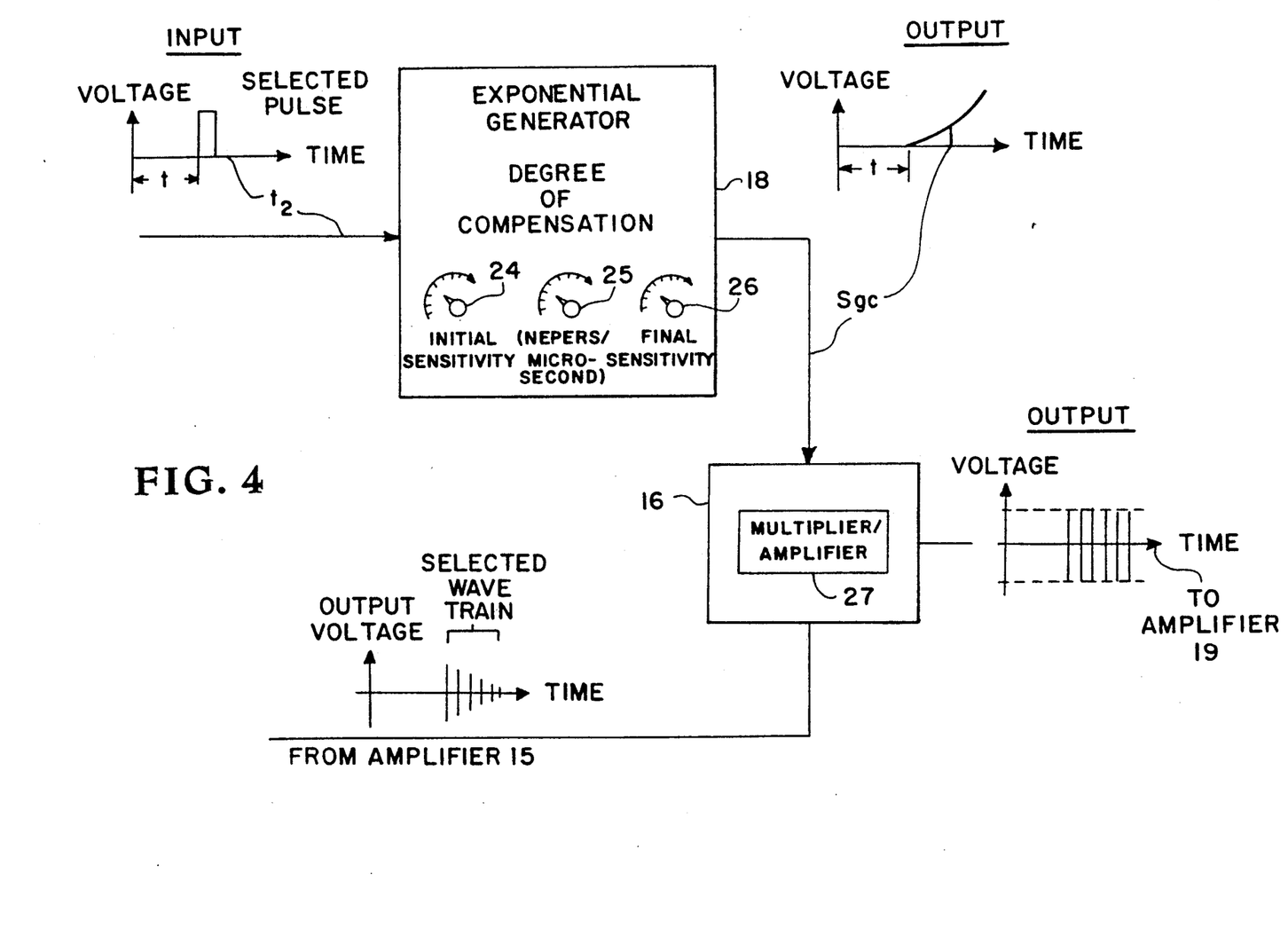
FIG. 4 is a schematic illustrating the adjustable exponential generator shown in FIG. 2 in greater detail.

As shown in FIG. 4 the characteristic of the exponential ramp signal Sgc may be incrementally adjusted with starting, maximum, and intermidiate (exponential adjust) gain controls 24, 25, and 26. The maximum gain control 26 is set so that the ramp signal Sgc does not drive a high speed multiplier and amplifier 27 in the time-gain componsation circuit 18 to saturation. The initial gain control 24 is set so that the amplitude A of the electrical signal $E_1$ is easily discernible. This may be effected when the interface causing the reflected pulse $R_1$ is either at unburned or burned skin. The intermediate gain control 25 is adjusted to vary the ramp signal Sgc which drives the time gain-compensator 16 to bring the level or amplitude A of the signal $E_3$ to the same level as that of the signal $E_1$. The level of any intermediate signals $E_2$ or $E_s$ will also be increased by the same exponential ramp by an amount dependent upon the time of occurrence.

After this adjustment of the exponential generator 18 and time-gain compensator 16 has been completed and a pattern of reflected pulses $R_1$, $R_2$, $R_3$, and $R_s$ represented ty the electrical signals $E_1$, $E_2$, $E_3$, and $E_s$ is presented on the screen of the oscilloscope 14, the inconsequential signals $E_s$ are removed by the envelope circuit 20 which may be a pair of back-biased Shottkey diodes connected in a full wave configuration to rectify the signals $E_1$, $E_2$, $E_3$ and $E_s$ as shown. The back bias limits the level of the signals rectified to those greater than the back bias thus eliminating substantially all signals $E_s$ from the display pattern.

An r-c and diode detector and filter in the baseline reject circuit 21 having a fast rise time and a slower decay time smooths out the remaining signals $E_1$, $E_2$, and $E_3$ to obtain a uniform display without greatly affecting the display resolution.

BRIEF DESCRIPTION OF OPERATION

Assume that the circuit of FIG. 2 is to be used to measure the thickness of a deep dermal burn. The basic operational sequence of ultrasonic events of the circuit occurs as follows: The pulser 11 activates the transducer T to transmit a pulse of ultrasound through a medium, such as waterbath W into the skin. Then the transducer and circuit immediately switches to the receiving mode.

As the ultrasound encounters the various boundaries or interfaces, planes 1, 2, and 3 each reflects one of the ultrasound back toward the transducer T in a specific sequence. The first pulse in the sequence is the reflection $R_1$ from the interface between the skin and the medium. The second pulse $R_2$ comes from the interface between the necrotic skin tissue and the viable skin tissue. The third pulse $R_3$ comes from the dermis-fat interface. Other reflections $R_s$ that arise from subcutaneous structures and boundaries are not important in this application and are rejected as later explained.

The pulses $R_1$, $R_2$, and $R_3$ are received by the transducer T and converted into corresponding voltage pulses or signals $E_1$, $E_2$, and $E_3$. The signals $E_1$, $E_2$, and $E_3$ are displayed on the screen of ocilloscope 14 in the same sequence in which received, the distance the signals being proportional to the time difference between their reception.

If the measurement is of healthy skin or, in some cases, full thickness burns, then a sequence of two pulses $R_1$ and $R_3$ or $R_2$ occurs producing the signals $E_1$ and $E_3$ or $E_2$ from the front surface of the skin and the dermis-fat interface respectively. Records of the respective resulting displays as the transducer T is scanned over the burned and adjacent unburned areas of skin also establish the front and back surface (planes 1 and 3). It is important that the transducer T is maintained substantially perpendicular to and at the same distance from the skin surface scanned.

Figure 8A:
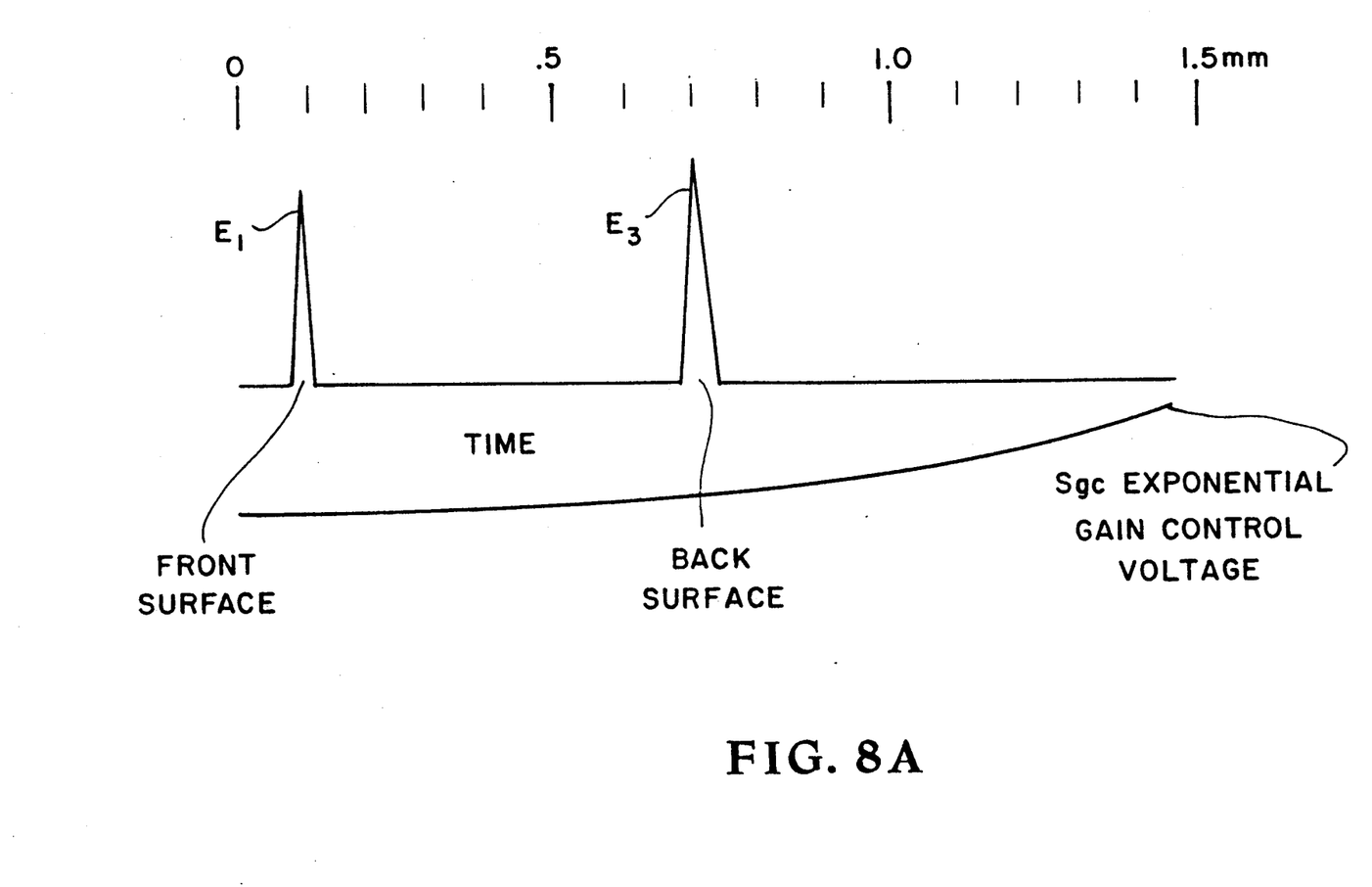
FIGS. 8A, B, and C illustrate typical displays using the invention to measure reflections in normal human skin, a second degree burn, and a full thickness burn, respectively.

FIG. 8A illustrates a typical display on oscilloscope 17 of ultrasonic reflections $R_1$ and $R_3$ measured in normal skin in practicing the invention, the first corresponding electrical signal $E_1$ being from the front surface and the next reflection signal $E_3$ being from the back surface. The exponential curve corresponds to the output signal Sgc from the exponential generator 18. The scale shown in millimeters permits a direct reading of skin thickness, in this instance 0.55 mm.

Figure 8B:
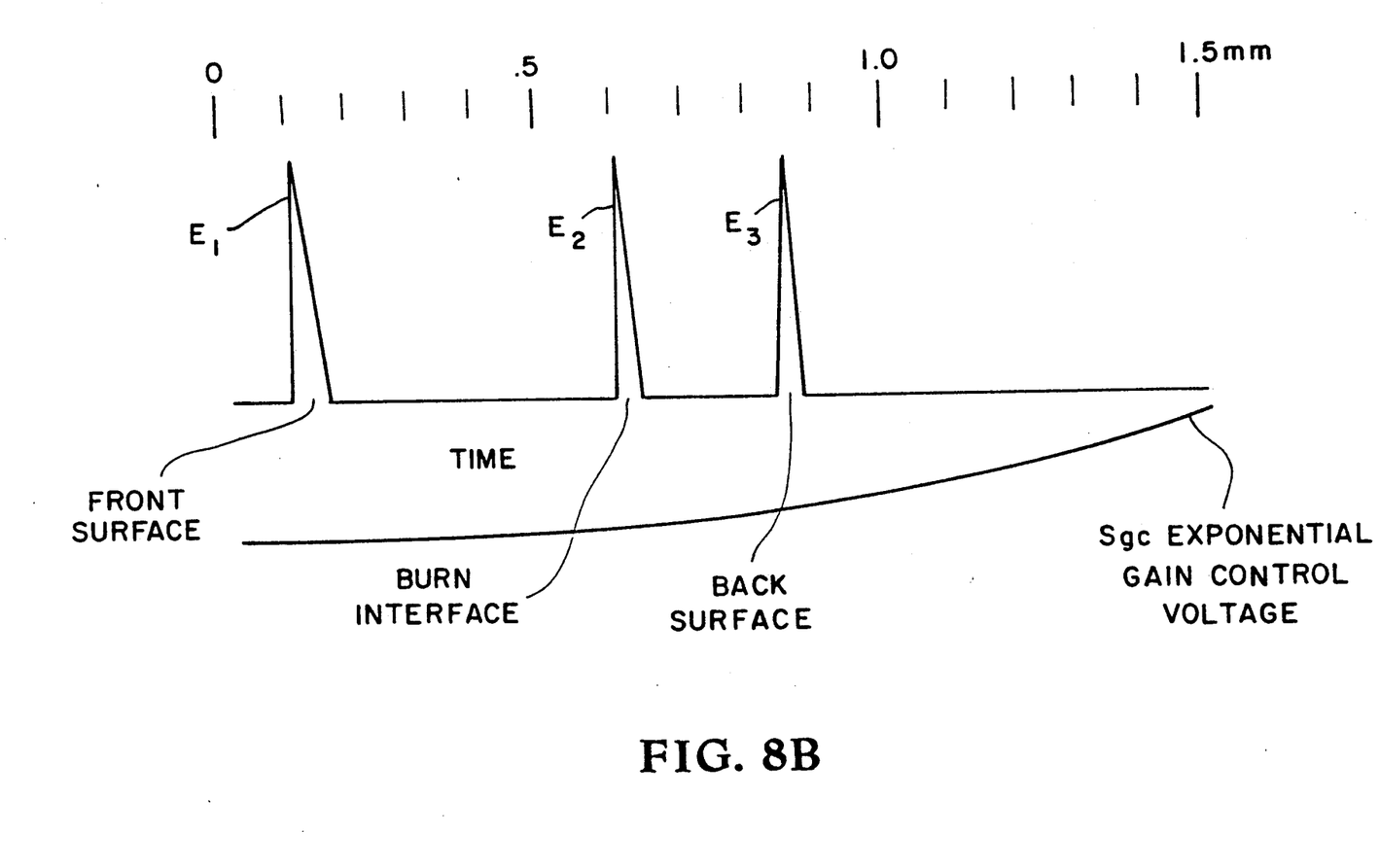

FIG. 8B illustrates typical ultrasonic reflections $E_1$, $E_2$, and $E_3$ from a second degree chemical burn as displayed in practicing the invention. As shown skin thickness measured from the front surface ($E_1$) and to the burn interface ($E_2$) equals 0.45 mm while the total skin thickness measured from the front surface ($E_1$) to the back surface ($E_3$) is 0.70 mm. The remaining viable skin between $E_2$ and $E_3$ is 0.25 mm. As shown the amplitudes of the respective signals $E_1$, $E_2$, and $E_3$ are substantially equal having again been characterized by exponentially increasing the gains of the signals $E_2$ and $E_3$ with the output signal Sgc.

Figure 8C:
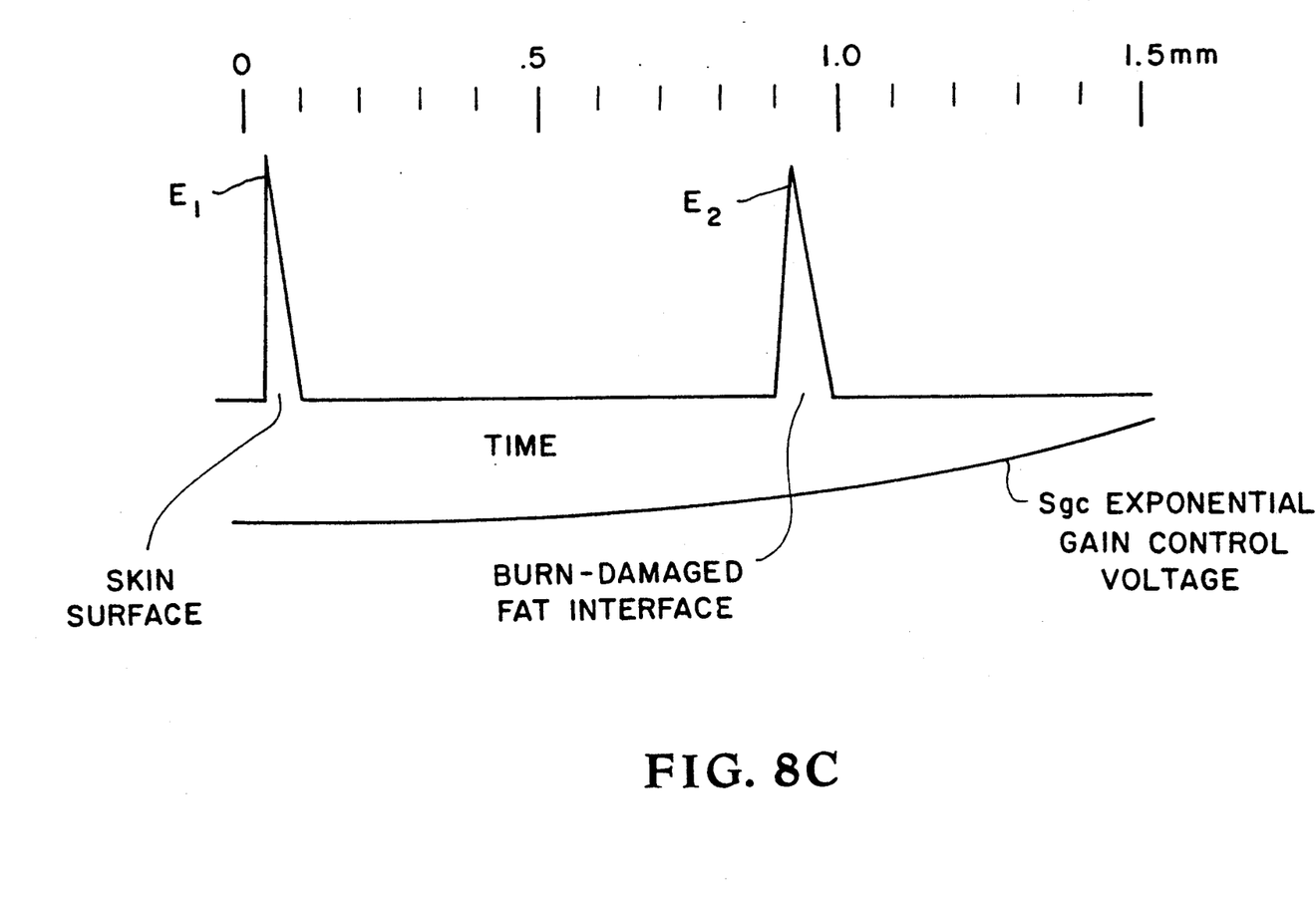

FIG. 8C illustrates a typical display of a full thickness using the invention as shown by the displayed signals $E_1$ and $E_2$, the distance between the skin surface ($E_1$) and the burn damaged dermis/fat surface interface is 0.75 mm.

While preferred embodiment have been described in detail, numerous modifications and changes may be made within the principles of the invention which is to be limited only by the appended claims.

What is claimed is:

1. The method of characterizing the amplitudes of a sequence of two or more ultrasonic pulses resulting from a main ultrasonic pulse transmitted from an acoustical transducer into a propagation medium and reflected from two or more impedence discontinuities having substantially the same coefficients of reflection in said propagation medium and in which the attenuation coefficient and velocity of tthe reflected pulses in said propagation medium remain substantially unchanged comprising the steps of:
    receiving and converting said sequence of reflected ultrasonic pulses into corresponding electrical signals;
    exponentially adjusting the amplitudes of said corresponding electrical signals to substantially the same and equal values of the amplitudes of the reflected pulses at the instant of their reflection; and
    thereafter displaying said corresponding electrical signals of substantially the same amplitude to locate said impedance discontinuities having substantially the same coefficients of reflection in said propagation medium.

2. The method of measuring the depth of a skin burn in human tissue formed of an epidermis covering a dermis layer overlying a subcutaneous layer of fat by characterizing the amplitude of a sequence of ultrasonic pulses $R_1$, $R_2$, and $R_3$ reflected by impedance discontinuities at interfaces between said epidermis and dermis, burned and unburned human tissue and the dermis and subcutaneous layer of fat respectively comprising the steps of:
    directing a main ultrasonic pulse of a known center frequency into said human tissue through an acoustical coupling;
    receiving and conveting said sequence of reflected ultrasonic pulses into a sequence of corresponding electrical signals $E_1$, $E_2$, and $E_3$ respectively;
    exponentially adjusting the amplitudes of said corresponding sequence of electrical signals $E_1$, $E_2$, and $E_3$ to substantially the same and equal values as representative of the amplitudes of the reflected pulses thereby restoring the respective amplitudes of said reflected pulses $R_1$, $R_2$, and $R_3$ to substantially their respective and relative values at the instant of their reflection; and
    thereafter displaying said sequence of corresponding electrical signals $E_1$, $E_2$, and $E_3$ of substantially the same amplitude to locate impedance discontinuities at said interfaces relatives to each other on a scale determined by the time interval of said sequence of ultrasonic pulses thereby measuring the depth of said skin burn in said human tissue.

3. The invention as defined in claim 1 wherein acoustical transducer is a focused transducer having a fixed center frequency selected from a range of values from 5 MHz to at least 50 MHz.

4. The invention as defined in claim 1 wherein the amplitudes of said corresponding electrical signals are adjusted during the time interval of said sequence of electrical pulses.

5. The invention of claim 1 wherein said sequence of reflected ultrasonic pulses includes first and third pulses $R_1$ and $R_3$ reflected from impedance discontinuities at a front and back surface of said propagation medium and a second pulse $R_2$ reflected from an impedance discontinuity in said propagation medium intermediate said front and back surfaces, said reflected pulses $R_1$, $R_2$, and $R_3$ therefter being converted into corresponding electrical signals $E_1$, $E_2$, and $E_3$.

6. The invention as defined in claim 2 wherein said acoustical transducer is a focused transducer having a fixed center frequency selected from a range of values from 5 MHz to at least 50 MHz.

7. The invention as defined in claim 2 wherein the amplitudes of said corresponding sequence of signals $E_1$, $E_2$, and $E_3$ are adjusted during the time interval of said sequence of said electrical signals.

8. The invention as defined in claim 2 wherein the amplitudes of the electrical signal $E_1$ is adjusted to a desired value and the amplitude of the electrical signals $E_2$ and $E_3$ thereafter exponentially adjusted to substantially equal the emplitude of the electrical signal $E_1$.

9. The invention as defined in claim 8 wherein the amplitudes of the electrical signals $E_2$ and $E_3$ are adjusted during the time interval of said sequence of electrical signals $E_1$, $E_2$, and $E_3$.

10. The invention as defined in claim 9 wherein the amplitudes of the electrical signals $E_2$ and $E_3$ are exponentially adjusted over a range of attenuation coefficient values for human skin varying in age from "young" to "old" as determined by the center frequency of said focused transducer.

11. Apparatus for characterizing the amplitudes of a sequence of ultrasonic pulses reflected from impedance discontinuities having substantially the same coefficients of reflection in a propagation medium in which the attenuation coefficient and velocity of the reflected pulses remains unchanged comprising:

acoustical transducer means;

means for coupling said transducer means to said propagation medium;

means for pulsing said transducer means to transmit a main ultrasonic pulse into said propagation medium and for receiving said sequence of reflected pulses resulting from said main pulse passing through said impedance discontinuities in said propagation medium;

circuit means for receiving and converting said sequence of reflected ultrasonic pulses into corresponding electrical signals;

exponential time-gain compensator means for characterizing the amplitudes of said electrical signals from said impedance discontinuities having subtantially the same coefficient of reflection in said propagation medium by adjusting them to substantially the same and equal value; and display means for displaying said characterized electrical signals to locate said impedance discontinuities in said propagation medium.

12. The invention as defined in claim 11 including timing circuit means for operating said exponential time-gain compensator means during the interval of said sequence of electrical pulses.

13. The invention as defined in claim 12 including envelope and reject circuit means connected to said exponential time-gain compensator means.

14. Apparatus for measuring the depth of a burn in human skin by characterizing a sequence of ultrasonic pulses $R_1$ and $R_3$ reflected from impedance discontiniuties at front and back surfaces of said skin respectively and a pulse $R_2$ reflected from a burned-unburned interface in said skin comprising:

transduce means including coupling means for transmitting a main pulse into said human skin and for receiving said sequence of reflected ultrasonic pulses $R_1$, $R_2$, and $R_3$ resulting therefrom;

means for sensing and converting said sequence of reflected pulses $R_1$, $R_2$, and $R_3$ into corresponding electrical signals $E_1$, $E_2$, and $E_3$;

time-gain compensator means for characterizing said reflected pulses $R_1$, $R_2$, and $R_3$ and said corresponding electrical signals $E_1$, $E_2$, and $E_3$ by exponentially adjusting the amplitudes of said electrical signals $E_1$, $E_2$, and $E_3$ to substantially the same value; and means for displaying said characterized electrical signals $E_1$, $E_2$, and $E_3$ and measuring selected distances therebetween.

15. The invention as defined in claim 14 including first and second timing means responsive to said transducer means and said sensing and converting means for initiating said time-gain compensator means and said display means.

16. The invention as defined in claim 15 wherein said time-gain compensator means is controlled by an exponential generator means controlled by said second timing means.

17. The invention as defined in claim 16 including envelope and reject circuit means series connected between said time-gain compensator means and said diplay means.

18. The invention as defined in claim 16 wherein said transducer means includes a focused transducer having a fixed center frequency and said exponential generator means controls said time-gain compensator means exponentially over a range of values determined by said fixed center frequency.

19. The invention as defined in claim 16 wherein said first timing means includes gating means for triggering said second timing means.

20. The invention as defined in claim 16 wherein said exponential generator means includes adjustment control means for selectively adjusting the amplitudes of said electrical signals $E_1$, $E_2$, and $E_3$ in said time-gain compensator means.

* * * * *